(12) United States Patent
Zhang et al.

(10) Patent No.: US 9,421,167 B2
(45) Date of Patent: Aug. 23, 2016

(54) PREPARATION OF MICROVESICLE-SIRNA COMPLEXES AND USE THEREOF IN AIDS TREATMENT

(75) Inventors: Chenyu Zhang, Beijing (CN); Ke Zeng, Beijing (CN); Hongwei Gu, Beijing (CN); Minghui Cao, Beijing (CN); Liming Li, Beijing (CN)

(73) Assignee: Micromedmark Biotech Co. Ltd., Beijing (CN)

( * ) Notice: Subject to any disclaimer, the term of this patent is extended or adjusted under 35 U.S.C. 154(b) by 700 days.

(21) Appl. No.: 13/700,062

(22) PCT Filed: Dec. 9, 2010

(86) PCT No.: PCT/CN2010/079602
§ 371 (c)(1),
(2), (4) Date: Apr. 26, 2013

(87) PCT Pub. No.: WO2011/147175
PCT Pub. Date: Dec. 1, 2011

(65) Prior Publication Data
US 2013/0203837 A1    Aug. 8, 2013

(30) Foreign Application Priority Data

May 26, 2010 (CN) .......................... 2010 1 0187578
May 26, 2010 (WO) ................ PCT/CN2010/073262

(51) Int. Cl.
*C12N 15/11* (2006.01)
*A61K 9/127* (2006.01)
*C12N 15/113* (2010.01)
*A61K 9/51* (2006.01)

(52) U.S. Cl.
CPC .............. *A61K 9/127* (2013.01); *C12N 15/111* (2013.01); *C12N 15/1131* (2013.01); *A61K 9/5184* (2013.01); *C12N 2310/14* (2013.01); *C12N 2320/32* (2013.01); *Y10T 428/2982* (2015.01)

(58) Field of Classification Search
CPC .. A61K 9/127; C12N 15/111; C12N 15/1131; C12N 2310/14
See application file for complete search history.

(56) References Cited

U.S. PATENT DOCUMENTS

2003/0124513 A1*    7/2003    McSwiggen .......... A61K 45/06
435/5

FOREIGN PATENT DOCUMENTS

| CN | 1426461 A | 6/2003 |
|---|---|---|
| CN | 1948475 A | 4/2007 |
| CN | 101432432 A | 5/2009 |
| CN | 101869715 A | 10/2010 |
| WO | 0182958 A2 | 11/2001 |
| WO | WO2005/032561 A1 * | 4/2005 |
| WO | 2005121369 A2 | 12/2005 |
| WO | 2007/126386 A1 | 8/2007 |
| WO | 2009100029 A1 | 8/2009 |
| WO | 2009147519 A1 | 12/2009 |
| WO | 2010111522 A2 | 9/2010 |

OTHER PUBLICATIONS

English Translation of CN1948475A (published Apr. 18, 2007) from ProQuest Dialog, pp. 1-20.*
English Translation of WO2005/032561A1 (published Apr. 14, 2005) from ProQuest Dialog, pp. 1-12.*
Jiang, Xue-yan et al. "In Vitro Study of RNA Interference on VIF Gene of HIV-1", Fudan Univ J Med Sci, vol. 36, No. 1 pp. 1672-8467 (Jan. 31, 2009).
International Search Report Written Opinion of PCT/CN2010/073262 date of mailing Jan. 13, 2011; Date of completion Jan. 4, 2011.
International Search Report of PCTCN2010/079602 date of mailing Mar. 17, 2011, date of completion Feb. 17, 2011.
Simpson, Richard J. et al. "Exosomes: Proteomic Insights and Diagnostic Potential", Expert Review of Proteomics, Future Drugs, London, GB, vol. 6, No. 3, pp. 267-283 (2009).
Wullner, Ulrich et al. "Targeted Delivery of Short Interfering RNAs—Strategies for In Vivo Delivery", Recent Patents on Anti-Cancer Drug Discovery, vol. 4, No. 1, pp. 1-8 (2009).
Extended European Search Report for corresponding EP Application 10852044.6 dated Dec. 6, 2013.

* cited by examiner

*Primary Examiner* — Brian Whiteman
(74) *Attorney, Agent, or Firm* — Thomas J. Engellenner; Reza Mollaaghababa; Pepper Hamilton LLP (57) ABSTRACT

The present invention provides drugs for treating AIDS, which comprises microvesicles carrying anti-HIV specific siRNA. The present invention also provides a preparation method of the drug.

24 Claims, 8 Drawing Sheets

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
gcccttcaga caggatcaga a                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
aagcagccat gcaaatgtta a                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
tcccagtagg agaaatctat a                                              21

```
<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
gcaagcttca caggaggtaa a                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
agatcctaga ctagagccct g                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
tggaagcatc caggaagtca g                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
gcatccagga agtcagccta a                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
tcaaagcaac ccacctccca a                                              21
```

PREPARATION OF MICROVESICLE-SIRNA COMPLEXES AND USE THEREOF IN AIDS TREATMENT

FIELD OF THE INVENTION

The present invention belongs to the field of drugs for the treatment of AIDS, specifically, RNA interference is used to treat AIDS. An efficient and specific siRNA and cellular microvesicles as a delivering vector are provided. The complex of the two can be used as a drug for treating AIDS and HIV infectors.

PRIOR ART

AIDS

AIDS, with a medical name of acquired immunodeficiency syndrome (abbreviated to AIDS), is a serious infectious diseases with high mortality. It is a kind of comprehensive immunodeficiency disease caused by human immunodeficiency virus (HIV) infection, which is mainly T cell immune function deficiency. It targets the most important T4 lymphocytes in the body's immune system and damages the T4 lymphocytes, thus destroying the whole body's immune system. The immune system in the body can assistant the attacks of various viruses when the human body is the normal state. Once the AIDS viruses invade the human body, the good defense system will be crumble and fall, thus various viruses will drive straight through blood and wound. In addition, some abnormal cells like cancer cells will also grow rapidly, reproduce and finally develop into various types of cancer. In general, AIDS virus cause death by destructing the human immune system and the resistance of the body, ultimately resulting in lose of resistance to various diseases.

HIV is RNA retrovirus with capsule, it belongs to the family of retroviridae, subfamily of lentiviruses, currently two types of HIV have been discovered, HIV-1 and HIV-2. HIV is a bi-layer structure with a spherical or oval shape and 100 nm to 150 nm in diameter. The core of the virus is located at the centre or off centre of the virion, which is composed of RNA, nucleocapsid protein (P7, P9), reverse transcriptase (RT), ribonuclease H (Ribo H) and integrase (INT); the viral capsid protein is outside the core, shows icosachedral symmetry and is composed of protein (P17/P18, P24/P25). The outermost layer of the virus is the membrane protein. There are 72 spikes on the envelop, containing glycoprotein gp120, and gP41 protein in bilayer of lipid.

After the AIDS virus entering the human body, it invades the human immune system directly, attacks and slaughter the T4 lymphocytes which is the most important and aggressive in the human immune system, thus making the body lose its ability to defense from starting. Once the AIDS virus enters the body, it is parasitic on the most core part of T4 lymphocytes and integrates with nucleus DNA into a single part, and replicates its own genetic materials using T4 lymphocytes. The propagation and replication of the virus damages and destroys the immune cells and release more viruses. The new propagated viruses infect more cells. In this way, the viruses replicate and propagate from generation to generation while the immune cells gradually died.

AIDS, which is transmitted by three contact routs: sex, blood and mother-to-child, is an infectious disease which is serious harm to health. AIDS has been found for only several decades from it is discovered up to now, however, the widespread epidemic caused by it has resulted in more than 30 million are infected and more than 10 million people lost their lives. There are million people infected with AIDS virus everyday.

Treatment Status of AIDS

Presently, drugs for anti-HIV treatment include: nucleoside reverse transcriptase inhibitors, non-nucleoside reverse transcriptase inhibitors, proteinase inhibitors and so on.

The action of the nucleoside reverse transcriptase inhibitors is to render the virus losing the template for replication by blocking reverse transcription of the viral RNA gene, i.e. blocking formation of the viral double-stranded DNA. These drugs firstly enter the infected cells and then form active triphosphate. AZT and d4T are analogues of deoxythymidine which is a natural substrate dT of viral nucleic acid replication; ddC and 3TC are analogues of deoxycytidine dC. These dideoxyribonucleoside triphosphates are competitive inhibitors of HIV-1 reverse transcriptase, when they are inserted into the growing DNA chain, they can cause the termination of the immature DNA chain and hindered synthesis of the viral DNA, thus resulting in the inhibition of the viral replication.

The non-nucleoside reverse transcriptase inhibitors are a group of compounds that inhibit the HIV-1 reverse transcriptase specifically which is irrelevant to nucleosides with totally different chemical structure. They are not competitive inhibitor of the substrate of HIV-1 reverse transcriptase, but inhibit reverse transcriptase by binding to the p66 hydrophobic region nearby the active site of the enzyme.

The proteinase inhibitors are compounds based on peptides, they either competitively inhibit the proteinase, activity or as the inhibitors complementing the active sites of proteinases, inhibit the function of the proteinase thus making the new synthesized viruses unable to mature.

Recently, the popular, highly active anti-retroviral therapy, so-called "cocktail therapy", is a method of using the proteinase inhibitors plus two kinds of nucleoside reverse transcriptase inhibitors to treat the infected person or patients. Such drug has strong effect of anti-virus, and viruses can not be detected in plasma after using them and the efficacy can be maintained for a long time. Furthermore, the human immune function destructed by AIDS virus may also be recovered completely or partially by this drug. But the therapy has its own limitation, including high cost, obvious side effect and the like.

Small Interfering RNA (siRNA)

Small interfering RNA (siRNA) is a kind of double-stranded RNA molecule consisting of more than 20 nucleotides, and it plays a role in silencing gene expression through the specific degradation of messenger RNA (mRNA). This process is called RNA interference (RNAi).

RNAi is a way of post-transcriptional regulation. siRNA can recognize its target gene specifically, and recruit the protein complexes which is called as RNA induced silencing complex (RISC). RISC, including RNase and the like, could inhibit gene expression specifically and efficiently through targeting cleavage of homologous mRNA. Since using RNAi technology can specifically knockout or turn off the expression of specific gene, RNAi technology is widely used in field of bio-medical research and treatment of various diseases.

Recently, using RNAs to treat AIDS has become a hot spot in the study of AIDS therapy. The viral genome can be degraded specifically by designing siRNA targeting HIV genome, could specifically decompose viral genome to kill the viruses from root. Researches have demonstrated that siRNA is able to inhibit the replication of HIV in cells cultured in vitro. HIV infection could be blocked by siRNA via inhibiting its own gene e.g., pie, gag, rev, tat and env) or its host gene (e.g, CD4, the major receptor of HIV) of HIV.

However, there are still some problems need to be solved, including lower transferring efficiency of siRNA and poor stability of siRNA etc. using siRNA for treating AIDS. Presently, the transferring of siRNA mainly use the way of vector carrying or antibody-conjugate. The vectors include liposome, nanocapsule, cyclodextrininclusion compound, etc. Although these vectors can prolong the drug retention time in vivo and increase the absorbing rate for siRNA drug in some extent, the targeting and efficacy of delivering the drugs still need to be improved, in spite of the coupling way of antibody conjugate can increase the targeting of siRNA, its stability in the body can not be guaranteed.

As a potential drug for treating AIDS patients and HIV infectors, RNAi is now facing some problems to be solved, poor specificity for delivering siRNA and lower efficacy are the main reasons limit its use.

Cellular Microvesicles (MVs)

Cellular microvesicles (MVs) are a category of biological vesicles with a lipid bi-layer membrane, ranging between 10-500 nm in size. They were first reported as early as in year 1967 and named "platelet dust" since they were derived from platelets, contain vesicles and have a role in promoting coagulation. In vitro studies, it has found that each of endothelial cells, vascular smooth muscle cells, platelets, leucocytes, lymphocytes, erythrocytes, and the like are all able to release MVs. According to their source, MVs can be divided into two categories: exosomes and shedding vesicles. Exosomes are secreted in the manner of exocytosis with multi-vesicular bodies (MVBs) in the case of cells are stimulated, and shedding vesicles are directly secreted from the cell surface by budding. Presently, different names are given to shedding vesicles secreted by different cells, for example, those from neutrophil granulocytes and monocytes are called ectosomes, and those from platelets are called microparticles. The membrane component of cellular MVs, depending on the cells from which they originate, is mainly composed of lipid and protein.

We have found through research that cellular MVs are derived from cells and have high affinity for organism, they are ideal carriers for drugs and thus they can be used in the RNAi method as carriers in the treatment of AIDS patients and HIV infectors to deliver siRNA efficiently and specifically.

Specifically, we have found that cellular MVs are carriers of biovesicle with highly effective rate and specificity in vivo. The membrane components (including specific surface receptors and membrane lipid structures) of cellular MVs secreted by different cells are the same as the plasma membrane components of the corresponding cells. Therefore, cellular MVs carrying receptor proteins or membrane lipid structure from the surface of the cells, have high affinity for the corresponding target cells. Meanwhile, since the cellular MVs contain important protein required for siRNA providing its effect, using cellular MVs as a carrier for deliver siRNA, siRNAs can be efficiently and selectively delivered into its target cells/tissues, thus remarkably enhancing the regulation of cellular functions. Therefore, the cellular MVs can be used effectively in the treatment of AIDS due to cellular MVs (including the membrane lipid vesicular structures with characteristics similar to the cellular MVs, such as exosomes and shedding vesicles as well as particular shedding vesicles secreted by different cells) have the advantages that they can increase the specificity, targeting and stability of siRNA delivery and promote the active effect of siRNA etc.

Therefore, the present invention provides a method of using cellular MVs for delivering siRNA targeting HIV genuine, the present invention also relates to cellular MVs-anti-HIV specific siRNA complex, preparation methods and uses in the treatment of AIDS and HIV infectors thereof.

DISCLOSURE OF THE INVENTION

The present invention provides a drug complex for treating AIDS, which can be use to deliver drugs for treating AIDS efficiently. The drug complex is a complex of siRNA and cellular MVs, including siRNA targeting HIV virus genuine and cellular MVs as a vector.

The HIV virus includes two types: HIV-1 and HIV-2.

Preferably, the HIV virus is HIV-1.

The siRNA includes all siRNA sequences being able to target HIV genome and cause specific degradation of HIV genome.

Preferably, the siRNA sequence is one or more of the following sequences:

```
                                          (SEQ ID NO: 1)
1) HIV-G1: GCCCTTCAGACAGGATCAGAA (SEQ ID NO: 2)
2) HIV-G2: AAGCAGCCATGCAAATGTTAA (SEQ ID NO: 3)
3) HIV-G3: TCCCAGTAGGAGAAATCTATA (SEQ ID NO: 4)
4) HIV-G4: GCAAGCTTCACAGGAGGTAAA (SEQ ID NO: 5)
5) HIV-T1: AGATCCTAGACTAGAGCCCTG (SEQ ID NO: 6)
6) HIV-T2: TGGAAGCATCCAGGAAGTCAG (SEQ ID NO: 7)
7) HIV-T3: GCATCCAGGAAGTCAGCCTAA (SEQ ID NO: 8)
8) HIV-T4: TCAAAGCAACCCACCTCCCAA
```

The cellular microvesicles (MVs) include natural biologic vesicles with a lipid bi-layer membrane, ranging between 10-500 nm in size, which is excreted from cells, for example by the way of cell budding and exocytosis, including structures of exosome, shedding vesicles as well as shedding vesicles secreted by different cells.

The relationship between the cellular MVs and siRNA is encapsulate and encapsulated.

The cellular MVs-siRNA complex is excreted by host cells expressing siRNA.

The host cells include all existing cell lines, cell strain and the primary cultures of cells/tissues of healthy human or patients with diseases.

The present invention provides a method for preparing the above-mentioned cellular MVs-siRNA complex drug.

The complex drug includes siRNA targeting HIV virus genuine and cellular MVs as a vector.

The method for preparing a drug includes transferring siRNA into host cells and purifying the cellular MVs carrying siRNA from cells.

The method for transferring siRNA into host cells includes the following three methods: 1) transfecting the mature siRNA manually synthesized using liposome; 2) transfecting a viral vector or plasmid carrying siRNA expression sequence using liposome or electroporation; and 3) establishing the cell lines permanently expressing siRNA.

Preferably, the method for transfecting the mature siRNA manually synthesized using liposome includes the following steps:
1) designing siRNA sequence targeting HIV virus genome;
The siRNA includes all siRNA sequences being able to target HIV genome and cause specific degradation of HIV genome. The designing method refers to the common method in the art form. Preferably, the siRNA sequence is one or more of the following sequences:

```
                                          (SEQ ID NO: 1)
i. HIV-G1: GCCCTTCAGACAGGATCAGAA (SEQ ID NO: 2)
ii. HIV-G2: AAGCAGCCATGCAAATGTTAA (SEQ ID NO: 3)
iii. HIV-G3: TCCCAGTAGGAGAAATCTATA (SEQ ID NO: 4)
iv. HIV-G4: GCAAGCTTCACAGGAGGTAAA (SEQ ID NO: 5)
v. HIV-T1: AGATCCTAGACTAGAGCCCTG (SEQ ID NO: 6)
vi. HIV-T2: TGGAAGCATCCAGGAAGTCAG (SEQ ID NO: 7)
vii. HIV-T3: GCATCCAGGAAGTCAGCCTAA (SEQ ID NO: 8)
viii. HIV-T4: TCAAAGCAACCCACCTCCC
```

2) synthesizing siRNA artificially according the sequence that has been designed;
3) transferring the siRNA into cells using liposome.

Preferably, the method for transfecting the viral vector or plasmid carrying siRNA expression sequence using liposome or electroporation includes the following steps:
1) designing siRNA expression sequence targeting HIV virus genome;
The expression sequence includes any one or more of the reverse complementary sequences of siRNA targeting HIV genome.
2) synthesizing a expression sequence artificially according the sequence that has been designed;
3) inserted the expression sequence into viral vector or plasmid which is suit for its expression;
4) transferring the recombinant viral vector plasmid into host cells using liposome or electroporation;
5) expressing the siRNA in cells by siRNA expression vector.

Preferably, the method for establishing the cell lines permanently expressing siRNA includes:
1) designing siRNA expression sequence targeting HIV virus genome;
2) constructing siRNA expression vector; Preferably, the vector is a lentivirus vector;
3) for recombinant plasmid which has correct sequence, extracting and purifying the high quality recombinant plasmid without endotoxin;
4) cotransfecting 293T cells with efficient recombinant vector (liposome) and recombinant plasmid for virus packaging and production; collecting the virus solution;
5) concentrating and purifying the virus solution;
6) detecting viral titers using GFP fluorescence method;
7) infecting the host cells with high quality virus solution;
8) detecting the gene function or the silencing efficiency of siRNA;
9) screening the stably transfected cell lines using antibiotics;
10) establishing permanently expressed transgenic monoclonal cell lines;

The host cells include all existing cell lines, cell strain and the primary cultures of tissues/cells of healthy human or patients with diseases.

The method for purifying the cellular MVs carrying siRNA includes the following steps:
1) collecting the culture medium of cell into which siRNA has been transferred;
2) separating and purifying the cellular MVs therein us certain methods.

The method for purifying cellular MVs includes one or more of differential centrifugation, immune-adsorption and ultrafiltration.

Preferably, the preparation method is differential centrifugation, for example, differential centrifugation including the following steps: (1) centrifuging cells or tissues at 300 g for 5 min, then collecting the supernatant; (2) centrifuging the supernatant of step (1) at 1500 g for 20 min, then collecting the supernatant; (3) centrifuging the supernatant of step (2) at 10000 g for 30 min then collecting the supernatant; (4) centrifuging the supernatant of step (3) at 110000 g for 70 min. and collecting the precipitate, i.e. the cellular MVs.

Or preferably, the preparation method is immune-adsorption, for example, immune-adsorption including the following steps: (1) first of all, centrifuging the cells or tissue at 3000 rpm for 30 min, then collecting the supernatant; (2) incubating the cell-specific antibodies or immune-magnetic beads absorbed on the petri dishes with the supernatant for 30-60 min and recovering the absorbed cellular MVs.

Or preferably, the preparation method is ultrafiltration, for example, ultrafiltration including the following steps: (1) first of all, centrifuging cells or tissue at 3000 rpm for 30 min, then collecting the supernatant; (2) placing the supernatant in an concentrated centrifuge tube having a filter membrane with certain pore diameter and then centrifuging at 4000 rpm and concentrating to achieve the cellular MVs.

The present invention also provides the use of the complex drug in the treatment of AIDS therapy.

The treatment of AIDS or HIV carriers using the complex drug of the present invention can be achieved using the method comprising the following steps:
1) injecting the above-mentioned complex drug into receptor or adding it into the receptor cells;
2) blocking the onward of HIV virus by siRNA mediated silencing effect;
3) optionally, detecting the content of HIV, i.e. detecting the effect of treatment for AIDS with the complex drug;

The receptor contains AIDS patients and/or HIV carriers.

The receptor cell contains all cell lines infected with HIV, as well as the primary cultures of tissues/cells of AIDS patients and HIV carriers.

The method for detecting the content of HIV includes nucleic acid detection of virus, P24 antigen assay, etc.

Preferably, the nucleic acid detection of virus is that detecting the content of HIV with PCR method (Real-time PCR), which includes the following steps: 1) extracting the viral RNA; 2) conducting reverse transcription (RT) of HIV RNA, and then amplifying the product cDNA thereof by PCR. According to the CT value in PCR, the original template size of viral cDNA involved into the reaction is derived, and then the content of virus is obtained.

Preferably, P24 antigen assay is that P24 antigen is detected using enzyme hated immune-sorbentassay (ELISA): usually using sandwich ELISA, that is, the purified known antibody is coated on the bottom of solid-phase reaction plate, after the serum is added, if p24 antigen is contained in serum, it will form antigen-antibody complex with the coated antibody. Then antibodies labeled with enzyme (HPR) are added, after color development by adding a substrate, the OD value of the reaction product is detected by ELIASA. In a certain range, since the OD value is linearly related to P24 antigen content, the content of virus can be reflected visually through the CD value.

EXAMPLES

It can be understood that the specific embodiments described herein are illustrated by way of examples and does not as a limitation of the invention. The main features of the present invention can be applied in various embodiments without departing from the scope of the invention. It will be realized or can be confirmed by a person skilled in the art that many equivalents can be applied to the specific steps described herein using conventional experiments. These equivalents are considered to be within the scope of the invention and covered by the appended claims.

Example 1

Transfecting the Mature siRNA Synthesized

In this example, the synthesized mature siRNA is transfected into cells, specifically including the following steps:
1) designing siRNA sequence targeting HIV-1 genome, in particular, we have designed eight siRNA sequences targeting the conservative regions of gag and tat genes of HIV-1 genome:

```
HIV-G1:  GCCCTTCAGACAGGATCAGAA    (SEQ ID NO: 1)

HIV-G2:  AAGCAGCCATGCAAATGTTAA    (SEQ ID NO: 2)

HIV-G3:  TCCCAGTAGGAGAAATCTATA    (SEQ ID NO: 3)

HIV-G4:  GCAAGCTTCACAGGAGGTAAA    (SEQ ID NO: 4)

HIV-T1:  AGATCCTAGACTAGAGCCCTG    (SEQ ID NO: 5)

HIV-T2:  TGGAAGCATCCAGGAAGTCAG    (SEQ ID NO: 6)

HIV-T3:  GCATCCAGGAAGTCAGCCTAA    (SEQ ID NO: 7)

HIV-T4:  TCAAAGCAACCCACCTCCCAA    (SEQ ID NO: 8)
```

2) synthesizing the above-mentioned mature siRNA artificially.
3) transfecting siRNA into embryonic kidney epithelial cell line 293T cell (American Type Culture Collection, ATCC) by liposome (Lipofectamine 2000, Invitrogen, US), specifically including the following steps:
   (1) 293T cells are cultured in the high concentration of glucose DMEM medium (Gibco, US) supplemented with 10% fetal calf serum (FBS) (Gibco, US), 5% $CO_2$, at 37° C.
   (2) 30 μl lipofectamine 2000 and 600 pmol negative control siRNA (non-specific siRNA sequence synthesized randomly) are mixed with 1 ml OPTI-MEM (Gibco, US) respectively to form mixture A and B, then kept at room temperature for 5 min.
   (3) 30 μl lipofectamine 2000 and 600 pmol siRNA are mixed with 1 ml OPTI-MEM (Gibco, US) respectively to form mixture C and D, then kept at room temperature for 5 min.
   (4) mixture A is mixed with mixture B to form mixture E, kept for 20 min.
   (5) mixture C is mixed with mixture D to form mixture F, kept for 20 min.
   (6) mixture E and mixture F are added into the cells of control group and experimental group respectively, OPTI-MEM is added to 15 ml. Cultured with 5% $CO_2$ at 37° C.
   (7) normal culture medium is refreshed after 6 h.
   (8) the transfection is completed after 24-48 h, and samples can be collected.

Example 2

Transfecting Transient Expression Vector of siRNA Targeting HIV Genome

Figure 1:
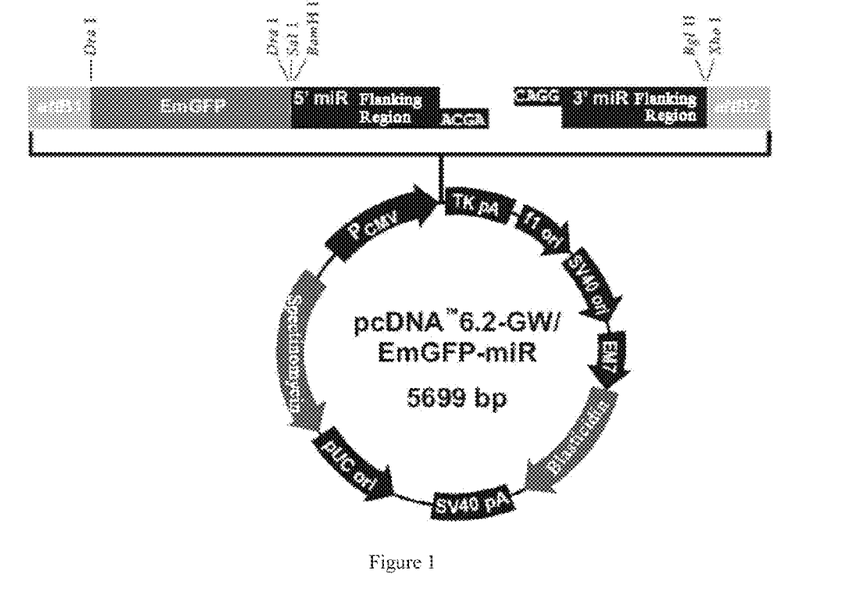
FIG. 1 shows the structural diagram of a transient expression vector.

In this example, the transient expression vector of siRNA is constructed by molecular biology method for expressing siRNA in the cultured cells, the method includes the following steps:
1) designing expression sequence of siRNA targeting HIV-1 genome in example 1;
2) synthesizing the above-mentioned expression sequence siRNA artificially, and inserting the synthesized sequence into eukaryotic expression vector pcDNA6.2 GW/EmGFP-miR (Invitrogen, US) of siRNA, and then constructing a recombinant vector. The schematic diagram of the expression vector is shown in FIG. 1.
3) transfecting the recombinant vector into the host cell 293T cell (American Type Culture Collection, ATCC) by liposome or electroporation.

The liposome transfection includes the following steps: (1) the cells in logarithmic growth phase are digested and collected with trypsin at 24 h before transfection, the cells are added into a 12-well plate with each well of 2 ml cell suspension at a density of $3 \times 10^5$ cells/well, incubated at with 5% $CO_2$ incubator. (2) after 24 h incubation, the cells can be used to transfection when its density achieving about 80%; (3) according to the instructions of Lipo-fectamine 2000 liposome, 3.0 µg vector used for transfection is added to 100 µl Opti-MEM without serum and antibiotics, mixed; (4) 2 µl liposome is added to 100 µl Opti-MEM, mixed gently and incubated under room temperate for 5 min; (5) the diluted plasmid and diluted Lipofectamine 2000 are mixed gently and incubated under room temperate for 20 min; (6) the mixture is added to each well of the 12-well plate with each well of 100 µl mixture, mixed gently; (7) after incubating at 37° C. with 5% $CO_2$ for 4-6 h, the culture medium comprising liposome and plasmid is replaced with DMEM culture medium containing 10% FBS, incubated at 37° C. with 5% $CO_2$ incubator; (8) the expression of the green fluorescent protein (GFP) is observed with an inverted fluorescence microscope, and the transfecting efficiency of the cells is counted for 80%.

The electroporation transfection includes the following steps: (1) cells growing to logarithmic growth phase are digested with trypsin and centrifuged at 4° C. under 1000 g for 5 min; (2) cells are resuspended with 0.5-fold volume of electroporation buffer to adjust the density of the cells to $3 \times 10^6$ cells/mL; (3) 30 µl vector DNA is added to 400 µl of cell suspension ($10^6$-$10^7$ cells), mixed gently with a pipet; (4) the mixture is added to the electro-transformation pool to ice bath. The electro-transformation pool is transferred to electrode to discharge for 1-2 min, and then the electro-transformation pool is placed in ice bath, after that the next step is performed immediately. (5) The electroporated cells are transferred to a Petri dish with a sterilized pipet tip, the complete culture solution of cells are added, incubated at 37° C. 5% $CO_2$ for observation of transfection efficiency; (6) the expression of GFP is observed with an inverted fluorescence microscope and the transfecting efficiency of the cells is counted for 75%.

Example 3

Establishing Transgenic Cell Lines Permanently Expressing siRNA

In order to obtain a stably expressed siRNA targeting HIV genome, in this example, the transgenic cell lines that can express siRNA permanently are established as follows: the permanent expression vector of siRNA is constructed and transfected into host cells; meanwhile, the permanently expressed clone in which the vector has been transferred into genome of the host cells is selected by screening and then monoclone cultured.

Figure 2:
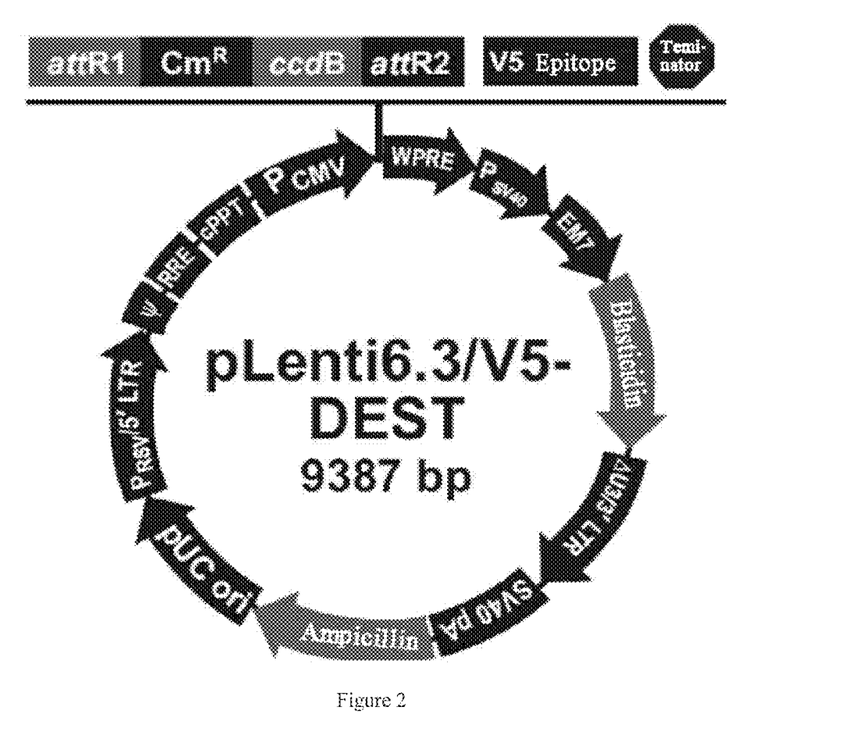
FIG. 2 shows the structural diagram of a permanent expression vector.

Specifically, the method includes the following steps:
1) synthesizing siRNA expression sequence targeting HIV genome in example 1;
2) constructing a lentiviral vector: inserting the synthesized sequence into a lentiviral vector pLeniti6.3/V5-DEST (invitrogen, US) to construct a recombinant vector. The schematic diagram of the vector is shown in FIG. 2;
3) packaging the lentivirus: transfecting 293T cells with recombinant vector to package the specifically including the following steps: 1. culturing 293T cells; 2. inoculating appropriate amount of cells in a 4×10 cm petri dish and incubating over night; 3. co-transfecting with a packaged plasmid (Invitrogen, US) and viral vector; 4. refreshing the medium and continue to culture; 5. collecting the viral solution; centrifuging for 10 min at 2000 g to remove cells and debris, and filtering with 0.45 µm filter membrane to obtain the viral stock. The viral stock is concentrated and re-suspended in 400 µm medium.
6. Detection of viral activity titer: HEK293 cells are inoculated in a 96-well plate; the viral solution is diluted using gradient dilution and added to the HEK293 cells. After 72 h, cells with GFP fluorescence are observed and the viral activity tier is calculated. HEK293 cells are incubated in DMEM medium (Gibco, US) supplemented with 10% FBS (Gibco, US) at 37° C. with 5% $CO_2$.
4) Virus infection and mono-clone positive clones screening, including the following steps: 1. culturing 293T cells to logarithmic phase; 2. inoculating appropriate amount of cells in petri dish, incubating overnight; 3. infecting 293T cells with lentivirus prepared prophase; 4. refreshing the medium, continue to culture; 5. screening with antibodies (using flow cytometry to sort the positive cells when necessary); picking out a number of monoclones to screen the positive clones; 6. amplifying the cells to adequate amount.

Example 4

Separating and Purifying Cellular MVs Carrying siRNA

SiRNA in cells could be encapsulated by cellular MVs excreted by cells, thus being released to the extracellular environment. By collecting the cell culture medium, and then subjecting to a series of separation and purification, the cellular MVs carrying siRNA, i.e. cellular MVs siRNA complex can be obtained.

In this example, cellular MVs carrying siRNA secreted by cells into which siRNA have been transferred are separated using the following methods respectively:
(1) Differential centrifugation: centrifuging the cultured cells under 300 g, 1500 g and 10,000 g successively to remove various types of cells and debris. Then centrifuging the supernatant under 110,000 g for 70 min and collecting the precipitate, i.e. the cellular MVs carrying siRNA secreted by cells.
(2) Immune-adsorption: adsorbing cell specific antibodies on the petri dishes or incubating serum/plasma or cell culture medium in which various types of cells and fragments have been removed with petri dish or immune-magnetic beads directly (for 30 min or 1 h). Cellular MVs of different cells could be absorbed and recovered directly.
(3) Filtration: Centrifuging serum/plasma or cell culture medium in which various types of cells and fragments have been removed in an concentrated centrifuge tube with a 100 KDa filter membrane at 4000 rpm and concentrating the precipitate to achieve the cellular MVs.

The isolated and obtained cellular MVs are observed under transmission electron microscope (TEM), including: the precipitates of the Cellular MVs are fixed with 2.5% glutaral at 4° C. overnight and rinsed for 3 times by PBS with 10 min each, then fixed with 1% of osmium tetroxide at room temperature for 60 min. The fixed samples are embedded with 10% of gelatin and then re-fixed with glutaral at 4° C. After that the samples are cut into small pieces (less than 1 mm³). The samples are dehydrated with increasing concentrations of ethanol solutions successively (30%, 50%, 70%, 90%, 95% and 100%×3). After embedded with epoxy resin, the samples are sliced with Leica UC6 ultramicrotome and then observed with FEI T20 TEM at 120 kV.

Figure 3:
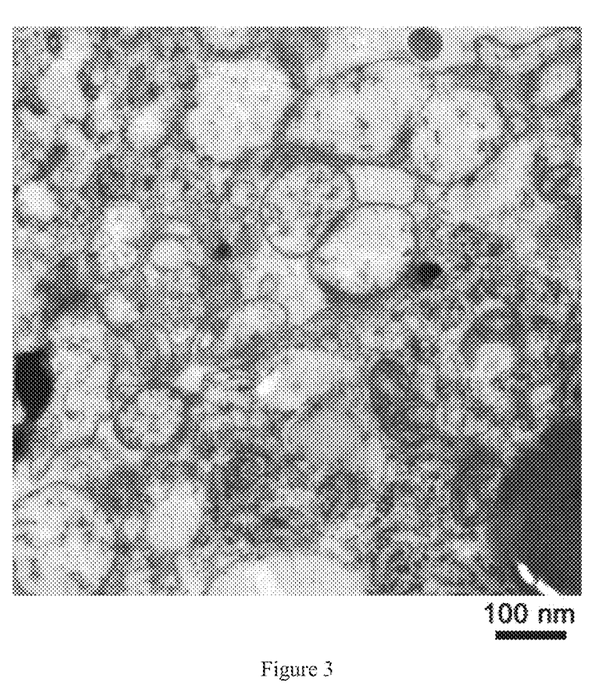
FIG. 3 shows the cellular MVs observed under the electron microscope.

The TEM picture of cellular MVs obtained by differential centrifugation is shown in FIG. 3, showing that the cellular MVs separated from the cultured cells are variable in size, ranging between 10-500 nm.

Example 5

Figure 4:
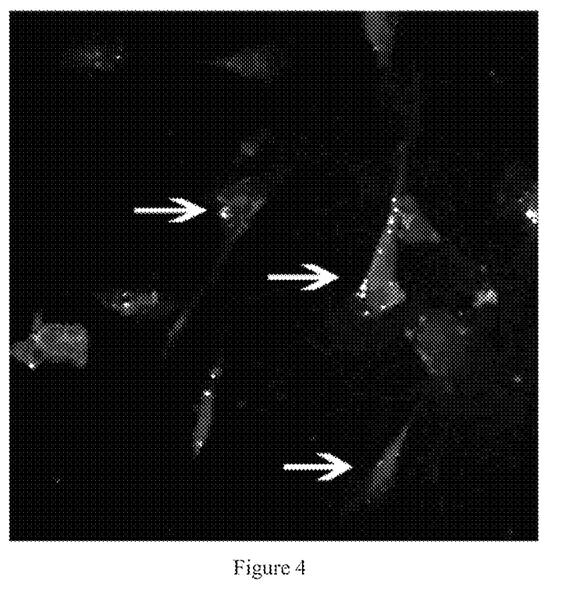
FIG. 4 shows 293T cells transfected with fluorescence-labeled siRNA.
Figure 5:
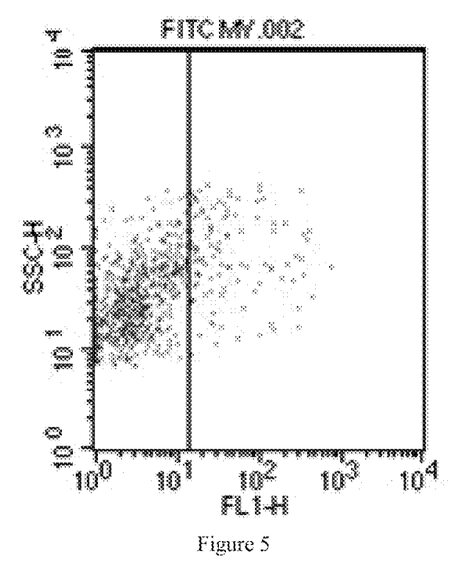
FIG. 5 shows the cellular MVs-siRNA complex detected by flow cytometry.

Identification of the Drug Complex Consisting of Cellular MVs and siRNA Carried Thereof In this example, a series of methods are used to detect the existence of the drug complex consisting of cellular MVs and siRNA carried thereof.
1) The fluorescence-labeled siRNAs are transfected into donor cells according to the method described in example 1. The result is shown in FIG. 4, it is observed under the fluorescence microscope that the fluorescence-labeled siRNA (bright spot pointed out by the arrow) had been transfected into cells.
2) Cellular MVs, excreted by donor cells transfected with fluorescence-labeled siRNA, are separated and identified according to the method described in example 4. The result is shown in FIG. 3. It is observed that the separated and obtained cellular MVs comply with the characteristics of cellular MVs from the shape, size and membrane structure, etc. (The characteristics see: Thery, C., Zitvogel, L., and Amigorena, S. (2002). Exosomes: composition, biogenesis and function. Nat Rev Immunol 2, 569-579. Cocucci, E., Racchetti, G. & Meldolesi, J. Shedding microvesicles: artefacts no more. *Trends Cell Biol* 19, 43-51 (2009)).
3) Flow cytometry is used to detect if there are any siRNA encapsulated in the microvesicles which had already been separated and purified as well as identified as cellular MVs, i.e. if they make up cellular MVs siRNA complex, the result is shown in FIG. 5. Due to siRNA is labeled with fluorescence, if siRNA is contained in cellular MVs, the cellular MVs must be labeled with fluorescence. Therefore, we use the flow cytometry to detect the content of fluorescence carried by cellular MVs. As it is shown in FIG. 5 that, most of the cellular MVs carry with fluorescence (right part of the vertical lines in FIG. 5), which proves siRNAs are encapsulated in cellular MVs, i.e. proves the existence of cellular MVs-siRNA drug complex.

Example 6

Inhibition of HIV Pseudovirion Using Cellular MVs-siRNA Complex Drug In Vitro HIV pseudotype virus is a HIV-like virus which is constructed by HIV genome with the other the coat protein of low hazard virus, simulates modes of action of HIV but has greatly decreased harmfulness. Usually, method of preparing HIV pseudotype virus includes: constructing the recombinant plasmid of HIV gene and expressing other lower hazard viruses, such as recombinant plasmid of coat G-glycoprotein gene of herpes stomatitis virus; co-transfecting the mammal cells with two types of plasmids to achieve pseudotype-lentivirus.

In this example, the therapeutic effect of the complex drug on AIDS will be supported by detecting inhibition of cellular MVs-siRNA complex drug on HIV pseudotype virus.

The detailed experimental steps include: 1) constructing the transgenic cell lines permanently expressing siRNA according to the method described in example 3; 2) separating and purifying the cellular MVs carrying siRNA, i.e. cellular MVs-siRNA complex, excreted by transgenic cells according to the method described in example 4; 3) adding the complex drug into Hela (CD4-LTR/β-Gal) cells (American Type Culture Collection, ATCC) infected with HIV pseudotype, virus. The hela cells are incubated in high-glucose DMEM (Gibco, US) supplemented with 10% PBS at 37° C. with 5% $CO_2$. 4) detecting the viral titer to analyze the inhibition of the complex drug on HIV pseudotype virus.

Figure 6:
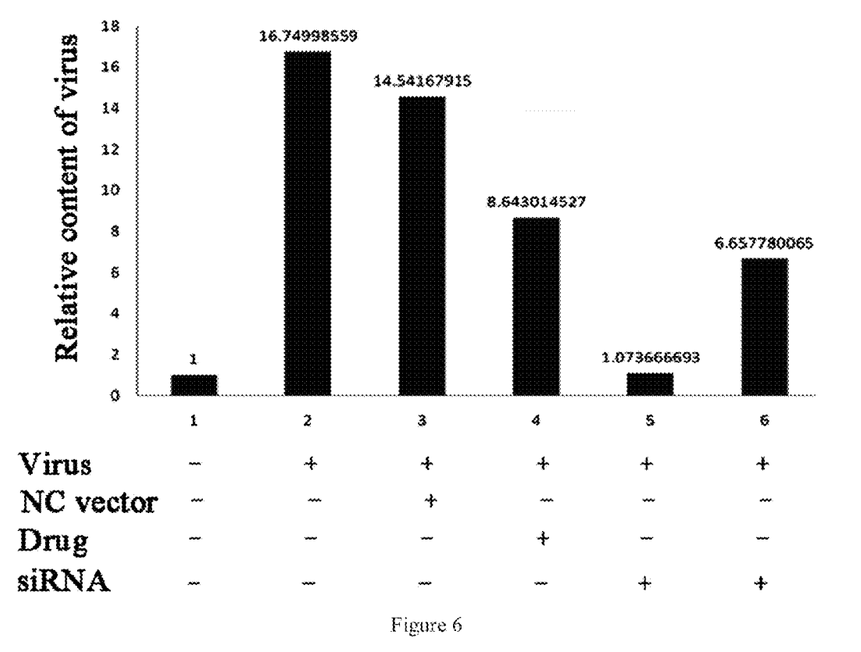
FIG. 6 shows the effect of the complex drug and the corresponding control on pseudotype virus.

The result is shown in FIG. 6. The ordinate represents the content of HIV pseudotypes in 293T cells. The blank cells completely freed of viruses are used as the control (horizontal axis 1 represents the column), its value is set to be 1; The content of pseudotype virus in cells only with viruses but without any therapeutic measures (horizontal axis 2 represents column) is more than 16 times of the control cells. However, adding the cellular MVs-siRNA complex drug as the treatment tool, the content of pseudotype virus in the host cells will dramatically decreased. It can be seen from the result that, after the drug is added (horizontal axis 5 and 6 represent columns), the content of pseudotype virus in host cells reduces to about 40% (horizontal axis 6 represents column). More importantly, adding the content of drugs (horizontal axis 5 represents column), the HIV pseudotype virus in host cells is even totally inhibited, and the content of HIV pseudotype virus decreases to the level that is equal to that of the non-pseudotype virus group (horizontal axis 1 represents column).

Furthermore, in order to determine the inhibitory effect of cellular MVs-siRNA complex drug on HIV pseudotype virus is caused by siRNA and not the cellular MVs, we have also transferred the cellular MVs without siRNA into host cells infected with HIV pseudotype virus as another control (horizontal axis 3 represents column). It can be seen from the result that only the cellular MVs can not have inhibitory effect on the HIV pseudotype virus, which has also demonstrated that it is the cellular MVs and not siRNA itself that have inhibitory effect on the viruses.

Meanwhile, we have also added an anti-AIDS drug with short peptides as the positive control (horizontal axis 4 represents column). It can be seen from the result that the content of HIV pseudotype virus can only be reduced to about 50% by the drug. Therefore, in compared with the conventional drugs for treating AIDS, the cellular MVs-siRNA complex drug has higher efficiency and better effect of inhibiting viruses.

Figure 7:
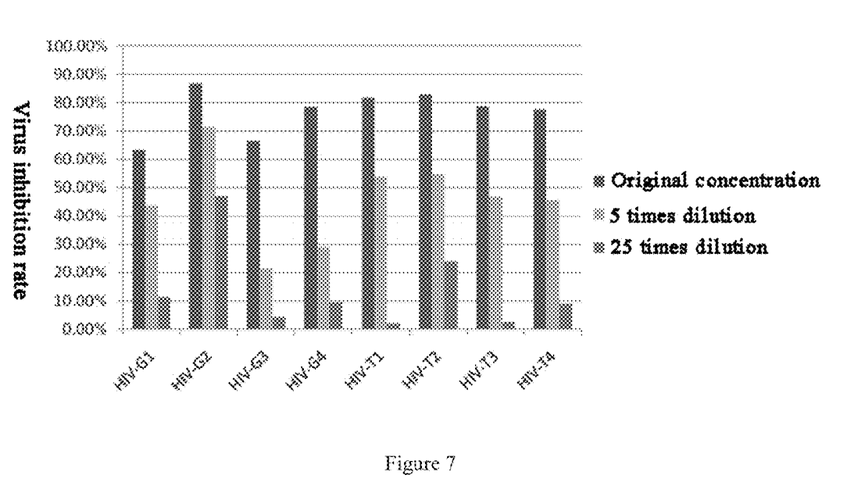
FIG. 7 shows the inhibition ratio of the complex drug corresponding to eight types of siRNA sequences on pseudotype virus.

The inhibition effect of the complex drug corresponding to all 8 siRNA sequences on HIV pseudotype virus in example 1 is shown in FIG. 7. It can be seen from FIG. 7 that the inhibition rate of all the drugs on HIV pseudotype virus achieves more than 60%, some even reach 86%. Meanwhile, the inhibition rate of the drugs on HIV pseudotype virus reduces with the decrease of the drug concentration.

The results prove that 8 cellular MVs-siRNA complex drugs have strong inhibition effect on HIV pseudotype virus and the effect is concentration-dependent and not accidental and random phenomena.

Example 7

Inhibition of Virus Using Cellular MVs-siRNA Complex Drug In Vitro

In this example, the inhibition effect of the complex drug corresponding to siRNA sequence HIV-T3 on HIV-1 virus is detected.

The detailed experimental steps include: 1) constructing the transgenic cell lines permanently expressing siRNA sequence HIV-T3 according to the method described in example 3; 2) separating and purifying the cellular MVs carrying siRNA, i.e. cellular MVs-siRNA complex, excreted by transgene cells according to the method described in example 4; 3) adding the complex drug into T cell leukemia cell line Jurkat cell (American Type Culture Collection, ATCC) infected with HIV-1 virus. The Jurkat cells are incubated in 1640 medium (Gibco, US) supplemented with 10% FBS at 37° C. with 5% $CO_2$. 4) detecting the viral titer to analyze the inhibition effect of the complex drug on HIV virus.

Figure 8:
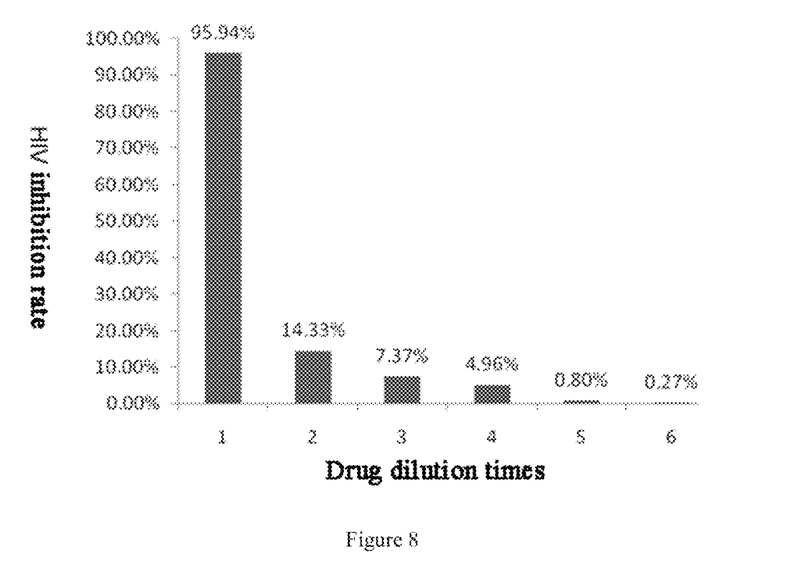
FIG. 8 shows the inhibition ratio of the complex drug HIV-T3 on pseudotype virus.

The result is shown in FIG. 8. It can be seen from the result that the complex drug corresponding to siRNA sequence HIV-T3 has strong inhibition effect on HIV-1 virus. When the original drug is added (column represented by horizontal axis 1), the inhibition rate of the drug on HIV-1 can reach 95.95%, while when the drug is diluted to 2 times gradient (column represented by horizontal axis 2 to 6), the inhibition rate of the drug on HIV-1 decreases accordingly.

The result further proves the inhibition of cellular MVs-siRNA complex drug on HIV virus in vitro, which establishes the foundation for the late development of the drug.

According to the above-mentioned methods, the inventors prove that, the above-mentioned cellular MVs-siRNA complex can be used as a drug and plays an action of inhibition effect on HIV virus. The mechanism of which is that: for the siRNA of HIV viral genome that can be transferred into target cells infected with HIV virus through cellular MVs efficiently and specifically, the inhibition effect on viruses can be achieved by cleavage action mediated by siRNA and specific for the viral genome.

The advantages of using siRNA for treating diseases are: siRNA plays a role as a recognizing signal by pairing with its target gene to recruit the silencing complex to cleave its target gene. Since the target of siRNA drugs is only its target gene, which does not interfere with the normal expression of the other genes, siRNA drugs have high specific and lower side effect. It has unique advantages using siRNA to treat AIDS, that is, due to the HIV viral genome is transferred as an exogenous genome into the RNA of human body, the inhibition of siRNA drugs on HIV virus can not affect the normal functions of the other cells of the human body at all, thus will not harm the human body.

Meanwhile, the advantages of using cellular MVs as a vector to deliver siRNA are: firstly, cellular MVs originate from cells, and is a native existence of organism, thus it can overcome the toxicity to cells and damage to the body of the drug carriers presently synthesized; secondly, various technical ways used during enclosing siRNA into cellular MVs are all easy to implement and the enclosing efficiency is very high, which increase its application potential in practical to a certain degree; more importantly, cellular MV are vesicle structures with a lipid hi-layer membrane and the structure of the outer membrane is similar to that of cytoplasm, which can enter the cell through fusion with the cell membrane and endocytosis. Meanwhile, cellular MVs would enter the target cells efficiently and selectively due to its surface carrying with molecule markers such as surface protein and various receptors/ligands originating from the surface of the cytoplasm of cells. If using the cellular MVs excreted from the primary culture of tissues or cells of patients themselves to enclose siRNA, immune rejection can be reduced and the transferring efficiency of the cellular MVs carrying siRNA to organism can be further improved. Based on the above-mentioned advantages, as a carrier to deliver the siRNA as a drug, cellular MVs will play a more important role in the development of drugs and prevention and treatment of the clinical diseases.

The invention claimed is:

1. A cellular microvesicles-anti-HIV specific siRNA complex, comprising at least one cellular microvesicle and at least one small interfering RNA (siRNA) sequence carried by the microvesicle, wherein the siRNA sequence is an anti-HIV specific siRNA sequence that includes the nucleic acid sequence GCCCUUCAGACAGGAUCAGAA (SEQ ID NO: 1).

2. The complex according to claim 1, wherein the cellular microvesicles are obtained from donor cells of human or animals.

3. The complex according to claim 2, wherein the donor cell includes at least one of a cell line and a primary cell culture.

4. The complex according to claim 2, wherein the cellular microvesicles are biologic vesicles structures.

5. The complex according to claim 1, wherein anti-HIV specific siRNA is encapsulated in cellular microvesicles.

6. The complex according to claim 1, wherein the mean diameter of the cellular microvesicles is 10-500 nm.

7. The complex according to claim 1, wherein the cellular microvesicles include at least one of an exosome and a shedding vesicle.

8. The complex according to claim 1, wherein the anti-HIV specific siRNA includes a siRNA sequence targeting HIV genome, and the anti-HIV specific siRNA causes specific degradation of HIV genome.

9. A pharmaceutical composition comprising the cellular microvesicles-anti-HIV specific siRNA complex according to claim 1 including the sequence GCCCUUCAGACAG-GAUCAGAA (SEQ ID NO: 1).

10. A method for treating AIDS, including: transferring the cellular microvesicles-anti-HIV specific siRNA complex according to claim 1 having into a cell, wherein the complex comprises at least one cellular microvesicle and at least one small interfering RNA (siRNA) sequence carried by the microvesicle, wherein the siRNA sequence is an anti-HIV specific siRNA sequence that includes the nucleic acid sequence GCCCUUCAGACAGGAUCAGAA (SEQ ID NO: 1).

11. The method according to claim 10, wherein the cell is in an AIDS patient or HIV carrier.

12. The method according to claim 10, wherein the cell is one of a cell line infected with HIV, and a primary culture of tissues/cells of an AIDS patient or HIV carrier.

13. A method of using cellular microvesicles-anti-HIV specific siRNA complexes in the preparation of a drug for treating AIDS or HIV infection, comprising the steps of:
  (1) designing an siRNA sequence that includes the nucleic acid sequence GCCCUUCAGACAGGAUCAGAA (SEQ ID NO:1) that targets an HIV virus genome;
  (2) artificially synthesizing the siRNA sequence or a DNA sequence encoding for expression of said siRNA sequence;
  (3) transferring the synthesized siRNA or expression sequence into host cells;
  (4) collecting a culture medium of the cells into which the siRNA has been transferred; and
  (5) isolating cellular microvesicles-anti-HIV specific siRNA complexes from the culture medium for use in a pharmaceutical composition.

14. The method of claim 13, wherein the step of transferring the siRNA into host cells further comprises transfecting said artificially synthesized mature siRNA into cells.

15. The method of claim 13, wherein the step of transferring the siRNA into host cells further comprises transfecting a viral vector or plasmid carrying said siRNA expression sequence into cells.

16. The method of claim 13, wherein the step of transferring the siRNA into host cells further comprises using a liposome or electroporation to transfecting the mature siRNA or expression sequence into the cells.

17. The method of claim 13, wherein the step of transferring the siRNA into host cells further comprises establishing one or more cell lines permanently expressing said siRNA.

18. The method according to claim 13, wherein the step of isolating the cellular microvesicles-anti-HIV specific siRNA complexes further comprises separating and purifying the complexes by performing at least one of a differential centrifugation, an immuno-adsorption and an ultrafiltration.

19. A method for preparing the cellular microvesicles-anti-HIV specific siRNA complexes according to claim 1, comprising the following steps:
  (1) designing an siRNA sequence that includes the nucleic acid sequence GCCCUUCAGACAGGAUCAGAA (SEQ ID NO:1) that targets an HIV virus genome;
  (2) artificially synthesizing the siRNA sequence or a DNA sequence encoding for expression of said siRNA sequence;
  (3) transferring the synthesized siRNA or expression sequence into host cells;
  (4) collecting a culture medium of the cells into which the siRNA has been transferred; and
  (5) isolating cellular microvesicles-anti-HIV specific siRNA complexes from the culture medium for use in a pharmaceutical composition.

20. The method of claim 19, wherein the step of transferring the siRNA into host cells further comprises transfecting said artificially synthesized mature siRNA into cells.

21. The method of claim 19, wherein the step of transferring the siRNA into host cells further comprises transfecting a viral vector or plasmid carrying said siRNA expression sequence into cells.

22. The method of claim 19, wherein the step of transferring the siRNA into host cells further comprises using a liposome or electroporation to transfecting the mature siRNA or expression sequence into the cells.

23. The method of claim 19, wherein the step of transferring the siRNA into host cells further comprises establishing one or more cell lines permanently expressing said siRNA.

24. The method according to claim 19, wherein the step of isolating the cellular microvesicles-anti-HIV specific siRNA complexes further comprises separating and purifying the complexes by performing at least one of a differential centrifugation, an immuno-adsorption and an ultrafiltration.

\* \* \* \* \*